United States Patent [19]

Mares et al.

[11] Patent Number: 5,531,998
[45] Date of Patent: *Jul. 2, 1996

[54] POLYCARBONATE-BASED BLOCK COPOLYMERS AND DEVICES

[75] Inventors: Frank Mares, Whippany; William J. Boyle, Jr., Denville; Reginald T.-H. Tang, Warren; Kundanbhai M. Patel, Landing; Abraham M. Kotliar, Westfield; Tin-Ho Chiu, Millburn, all of N.J.

[73] Assignee: United States Surgical Corporation, Norwalk, Conn.

[ * ] Notice: The term of this patent shall not extend beyond the expiration date of Pat. No. 4,920,203.

[21] Appl. No.: 162,814

[22] Filed: Dec. 3, 1993

Related U.S. Application Data

[60] Continuation of Ser. No. 843,116, Feb. 28, 1992, abandoned, which is a division of Ser. No. 134,339, Dec. 17, 1987, Pat. No. 5,120,802.

[51] Int. Cl.$^6$ .............................. A61K 9/70; A61L 17/00; A61L 31/00; A61L 15/00
[52] U.S. Cl. .................... 424/426; 424/443; 424/444; 428/35.7; 428/36.1; 428/280; 428/308.4; 428/397; 428/398; 428/399; 428/400; 606/231; 606/232; 623/7

[58] Field of Search ..................... 424/422, 426, 424/444, 78.17, 443–45; 514/772.7; 523/105; 428/36.1, 224, 359, 364–65, 412; 606/231–232; 623/1, 7, 13; 525/415, 937; 528/354

[56] References Cited

U.S. PATENT DOCUMENTS

| 3,301,824 | 1/1967 | Hostettler et al. | 260/77.5 |
| 4,243,775 | 1/1981 | Rosensaft et al. | 525/415 |
| 4,705,820 | 11/1987 | Wang et al. | 524/381 |
| 4,916,193 | 4/1990 | Tang et al. | 523/111 |
| 4,920,203 | 4/1990 | Tang et al. | 523/111 |
| 5,047,048 | 9/1991 | Bezwada et al. | 525/415 |
| 5,066,772 | 11/1991 | Tang et al. | 528/354 |
| 5,080,665 | 1/1992 | Jarrett et al. | 528/354 |
| 5,084,524 | 1/1992 | Leitz et al. | 525/415 |
| 5,120,802 | 6/1992 | Mares et al. | 525/415 |

FOREIGN PATENT DOCUMENTS

| 0202444 | 11/1986 | European Pat. Off. . |
| 1426964 | 12/1965 | France . |

*Primary Examiner*—Edward J. Webman

[57] ABSTRACT

This invention relates to a novel polycarbonate-based block polymer, and to fibers and bioresorbable implantable medical devices fabricated from said fibers.

23 Claims, No Drawings

POLYCARBONATE-BASED BLOCK COPOLYMERS AND DEVICES

This is a continuation of application Ser. No. 07/843,116 filed on Feb. 28, 1992, now abandoned, which is a division of U.S. application Ser. No. 07/134,339 filed Dec. 17, 1987 now issued as U.S. Pat. No. 5,120,802.

FIELD OF THE INVENTION

This invention relates to polycarbonate-based block copolymers having at least one flexible block and at least one block which is more crystalline than said first flexible block. The block copolymer so formed are particularly suited to be spun into fibers, extruded into films, tubings, and devices of many shapes and sizes. Devices made from the block copolymers are especially useful with regard to their biodegradability or bioresorption properties.

BACKGROUND OF THE INVENTION

Polycarbonates have been known for a number of years. U.S. Pat. No. 3,301,824 (1967) describes the preparation of carbonate homopolymers and random copolymers with lactones. The patent generally discloses the polymers as having utility in the molding, coating, fiber and plasticizer fields. There is no appreciation whatsoever of biodegradable devices composed in whole or in part of polycarbonate "biopolymers".

U.S. Pat. Nos. 4,243,775 (1981) and 4,429,080 (1984) disclose the use of polycarbonate-containing polymers in certain medical applications, especially sutures. However, this disclosure is clearly limited only to "AB" and "ABA" type block copolymers where only the "B" block contains poly (trimethylene carbonate) or random copolymer of glycolide with trimethylene carbonate, and the "A" blocks are necessarily limited to polyglycolide. The dominant portion of the polymers is necessarily the glycolide component.

Accordingly, the art has failed to appreciate the B potential biological or medical uses of block copolymers, having carbonates as their major component. This is especially true with respect to biodegradable or bioresorbable properties as well as the wide range of mechanical properties achieved with these materials for use in the fabrication of various devices.

Bioresorbable polymers have been used in the fabrication of devices for implantation in living tissue for several decades. Medical application of such polymers include absorbable sutures, haemostatic aids and, recently, intraosseous implants and slow-release drug delivery systems, to name but a few.

Use of such polymers has been extended to tissue regeneration devices such as nerve channels, vascular graft channels, sperm duct channels, fallopian tube ducts or channels and the like. To be effective, these devices must be made from materials that meet a wide range of biological and physical chemical prerequisites. The material must be bioresorbable at least in part, nontoxic, noncarcinogenic, nonantigenic, and must demonstrate favorable mechanical properties such as flexibility, suturability in some cases, and amenability to custom fabrication.

With particular emphasis on the replacement of injured, diseased, or nonfunctioning blood vessels, nonresorbable synthetic permanent vascular grafts have been available and are made of either Dacron (polyethylene terephthalate) or microporous Teflon (polytetrafluoroethylene). Various prostheses such as grafts, and especially those of small diameters for insertion in coronary bypass procedures, must have certain properties. These properties include physical and mechanical compatibility with the vessel to which they are connected, suturability, compliancy, ability so withstand pressure and pressure fluctuations, and flexibility. These properties also include biocompatibility—including such aspects as sterilizability and absence of toxicity, pyrogenicity, allergenicity, and mutagenicity; and adequate durability, both in terms of "shelf life" after fabrication and appropriate durability after implantation. Mechanical problems which can develop from the mismatch of a native vessel and a prostheses include elongation which results in, kinking, and perhaps in aneurysm formation and anastomotic hyperplasia. Vascular grafts of 8 mm in internal diameter or larger, made of biodurable materials, have so far been the only successful prostheses, providing a conduit for maintaining continuous blood flow while inflicting a minimized and clinically tolerable hemotologic trauma. Most vascular grafts made of Dacron in current clinical use are of knitted or woven nonbiodegradable Dacron fibers with open pores in the fabric which have to be closed or diminished by preclotting before implantation. Such prostheses have been used as vascular replacements, but only for the relatively larger arteries. While bioresorbable materials have been proposed for use in such prostheses, the practical use of bioresorbable materials are, in general, currently limited to temporary devices such as fasteners, specifically sutures and pins.

Additionally, there has been an appreciation in art of vascular prostheses, that macrophages infiltrate the implanted bioresorbable portion of the devices digest bioresorbable materials, and aid in the formation of organized tissue which is comparable to that of the intact tissue. In particular, macrophages can be induced to secrete elastin in this tissue-reforming process. Induction of elastin secretion in the tissue repair can be accomplished by maintaining a mechanically dynamic environment as opposed to a static environment. While the desirability of maintaining a mechanically dynamic environment has been recognized, the art has not provided materials suitable for implantation which have this capability.

SUMMARY OF THE INVENTION

The present invention provides a block copolymer comprising at least one crystalline or semi-crystalline "A" block, and at least one "B" block which is more flexible than the "A" block. The A block or blocks are rigid and, crystalline or semi-crystalline blocks formed from at least one type of recurring monomeric unit having the general Structures I and II:

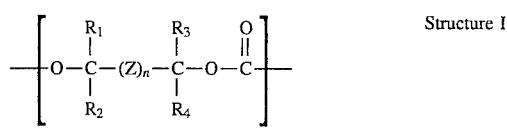

Structure I

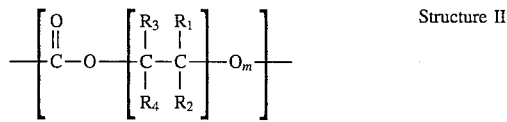

Structure II wherein:

Z is

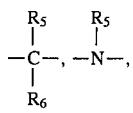

or a combination thereof where Z is selected such that there are no adjacent heteroatoms;

n and m are the same or different and are integers from about 1 to 8;

$R_1$, $R_2$, $R_3$, and $R_4$ are the same or different at each occurrence and are hydrogen, aryloxyalkyl, alkoxyaryl, aryloxyaryl, arylalkyl, alkylarylalkyl, arylalkylaryl, alkylaryl, arylcarbonylalkyl, alkyl, aryl, alkylcarbonylalkyl, cycloalkyl, arylcarbonylaryl, alkylcarbonylaryl, alkoxyalkyl, or aryl or alkyl substituted with one or more biologically compatible substituents such as alkyl, aryl, alkoxy, aryloxy, dialkylamino, diarylamino, alkylarylamino substituents;

$R_5$ and $R_6$ are the same or different at each occurrence and are $R_1$, $R_2$, $R_3$, $R_4$, dialkylamino, diarylamino, alkylarylamino, alkoxy, aryloxy, alkanoyl, or arylcarbonyl; or any two of $R_1$ to $R_6$ together can form an alkylene chain completing a 3, 4, 5, 6, 7, 8 or 9 membered alicyclic, fused, spiro, bicyclic and/or tricyclic ring system, which system may optionally include one or more non-adjacent carbonyl, oxa, alkylaza, or arylaza groups; With the proviso that at least one of $R_1$ to $R_6$ is other than hydrogen.

The B-block or blocks are formed of one or more recurring units derived from monomers such as carbonates, lactones, hydroxy carboxylic acids, cyclic anhydrides, dioxanones, lactides, epoxides, diols, cyclic ethers, dioxepanones, ortho esters, polyols, ortho carbonates, epoxides/$CO_2$, and the like.

Each "A" block and "B" block may comprise a single type of recurring monomeric unit. Alternatively, each block may comprise more than one type of recurring monomeric unit, randomly distributed throughout each block. For example, the block copolymers as described above may have repeating block units such as AB, ABA, BAB, ABAB, ABABA, BABAB, and the like, where each block and each "B" block contains the same or substantially the same types of recurring monomeric unit, and/or where each block contains the same or substantially the same number of recurring units. Alternatively, the various "A" and "B" blocks contained in the block copolymers may have more than one type of "A" block or "B" block, each of which may contain a different type or types of recurring monomeric units; or each block may contain the same or different types of recurring units but have differing number of recurring units in each block. For example, with respect to the recurring blocks of A's and B's, each of them may also be the same or different, i.e., ABABA may in fact be ABA'B'A", ABA may be ABA', ABA may be ABB'B"A or ABB'A'A", etc. Especially preferred are block copolymers of structures AB and ABA.

The present invention also provides a prosthetic device suitable for implantation into living tissue, said device formed from the block copolymers of the invention and capable of aiding in the regrowth and regeneration of living tissue. In particular, fibers may be formed from the block copolymers and woven into fabric for the fabrication of such devices, especially vascular grafts. The block copolymers of the invention are also particularly suited to be formed into other medical devices such as nerve channels, by conventional techniques.

Terms of art describing the various characteristics of the block copolymers of the invention and their uses are as follows.

As used herein, the term "block" means a sequence of one type of monomeric unit at least about 5 units long, or such sequence of two or more types of recurring monomeric units either randomly distributed in such a sequence or distributed such sequence in a block-like fashion. One block must be able to crystallize, at least partially, in any block copolymer containing at least two different types of blocks.

As used herein, the term "crystalline or hard block" means a sequence at least about 20 monomeric units long of a particular monomeric unit or such a sequence of two or more types of recurring monomeric units either randomly distributed throughout such sequence or distributed in such sequence in a block-type fashion which exhibits crystalline or partially crystalline properties, and which are characterized by exhibiting a melting point or a peak in a differential scanning calorimeter (DSC) no lower than about 37° C. (for applications relevant to physiological temperature). A crystalline polymer block may also be a random copolymer that is capable of crystallization as a block copolymer containing at least two different types of recurring units.

As used herein, the term "flexible, rubbery, or soft block" means a sequence at least about 5 units long of a particular monomeric unit, or such sequence of two or more types of recurring monomeric units either randomly distributed throughout such sequence or distributed in such sequence in a block-like fashion which is amorphous, and which is characterized by exhibiting a glass transition temperature below that of the application temperature, e.g., less than about 37° C., preferably less than about 32° C., and more preferably less than about 20° C. for medical applications relevant to physiological temperature.

DETAILED DESCRIPTION OF THE INVENTION

The block copolymers of the invention comprise two components, one of which is at least one unit of a crystalline or hard A block and the other is at least one flexible or amorphous "B" block. The "A" block or blocks are formed from at least one type of monomeric unit having the General Structures I and II:

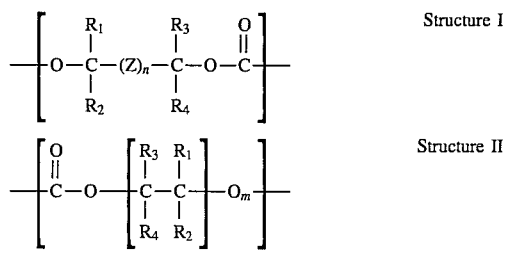

wherein:

Z is

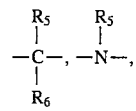

or a combination thereof where Z is selected such that there are no adjacent heteroatoms;

n and m are the same or different at each occurrence and are integers from about 1 to about 8;

$R_1$, $R_2$, $R_3$, and $R_4$ are the same or different at each occurrence and are hydrogen, aryloxyalkyl, alkoxyaryl, aryloxyaryl, arylalkyl, alkylarylalkyl, arylalkylaryl, alkylaryl, arylcarbonylalkyl, alkyl, aryl, alkylcarbonylalkyl, cycloalkyl, arylcarbonylaryl, alkylcarbonylaryl, alkoxyalkyl, or aryl or alkyl substituted with one or more biologically compatible substituents such as alkyl, aryl, alkoxy, aryloxy, dialkylamino, diarylamino, alkylarylamino substituents; and $R_5$ and $R_6$ are the same or different and are $R_1$, $R_2$, $R_3$ $R_4$, dialkylamino, diarylamino, alkylarylamino, alkoxy, aryloxy, alkanoyl, or arylcarbonyl; or any two of $R_1$ to $R_6$ groups together may form an alkylene chain completing a 3, 4, 5, 6, 7, 8 or 9 membered alicyclic, fused, spiro, bicyclic and/or tricyclic ring system, which system may optionally include one or more non-adjacent carbonyl, oxa, alkylaza, or arylaza groups; with the proviso that at least one of $R_1$ to $R_6$ is other than hydrogen.

Illustrative of useful $R_1$, $R_2$, $R_3$, and $R_4$, groups are hydrogen; alkyl such as methyl, ethyl, propyl, butyl, pentyl, octyl, nonyl, tert-butyl, neopentyl, isopropyl, sec-butyl, dodecyl and the like; cycloalkyl such as cyclohexyl, cyclopentyl, cyclooctyl, cycloheptyl and the like; alkoxyalkyl such as methoxymethylene, ethoxymethylene, butoxymethylene, propoxyethylene, pentoxybutylene and the like; aryloxyalkyl and aryloxyaryl such as phenoxyphenylene, phenoxymethylene and the like; and various substituted alkyl and aryl groups such as 4-dimethylaminobutyl, and the like;

Illustrative of other $R_1$ to $R_4$ groups are divalent aliphatic chains, which may optionally include one or more non-adjacent divalent carbonyl groups, oxa, alkylaza or arylaza groups to form alicyclic, fused, spiro, bicyclic and/or tricyclic ring systems, such as —(CH$_2$)$_2$—, —CH$_2$C (O)CH$_2$—, —(CH$_2$)$_3$—, —CH$_2$—CH(CH$_3$)—, —(CH$_2$)$_4$—, —(CH$_2$)$_5$—, —CH$_2$OCH$_2$—, —(CH$_2$)$_2$—N(CH$_3$)CH$_2$ —, —CH$_2$O(O)CH$_2$—, —(CH$_2$)$_2$—N(CH$_3$)—(CH$_2$)$_2$—, —CH(CH$_2$CH$_2$)$_2$CH—, —CH(CH$_2$CH$_2$CH$_2$)$_2$CH—, —CH(CH$_2$)(CH$_2$CH$_2$)CH—, —CH(CH$_2$)(CH$_2$CH$_2$CH$_2$)CH$_2$—, —CH(C(CH$_3$)$_2$(CH$_2$CH$_2$)CH—, and the like.

Illustrative of useful $R_5$ and $R_6$ groups are the above-listed representative $R_1$ to $R_4$ groups, including —OCH$_2$C(O)CH$_2$—, —(CH$_2$)$_2$—NCH$_3$—, —OCH$_2$C(O)CH$_2$—, —O—(CH$_2$)$_2$—O—; alkoxy such as propoxy, butoxy, methoxy, isopropoxy, pentoxy, nonyloxy, ethoxy, octyloxy, and the like; dialkylamino such as dimethylamino, methylethylamino, diethylamino, dibutylamino, and the like; alkanoyl such as propanoyl, acetyl, hexanoyl, and the like, arylcarbonyl such as phenylcarbonyl, p-methylphenylcarbonyl, and the like; and diarylamino and arylalkylamino such as diphenylamino, methylphenylamino, ethylphenylamino and the like.

Preferred for use in the practice of this invention are block copolymers comprising as a "A" block carbonate recurring units of General Structure I wherein:

Z is

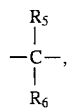

or a combination thereof where Z is selected such that there are no adjacent heteroatoms;

n is 1, 2 or 3; and $R_1$ to $R_6$ are as defined above, preferably where aliphatic moieties included in $R_1$ to $R_6$ include up to about 10 carbon atoms and the aryl moieties include up to about 16 carbon atoms.

Illustrative of these preferred copolymers are those in which the "A" block is formed from at least one type of recurring monomeric unit of the General Structure I wherein n is 1 and Z is of the formulae:

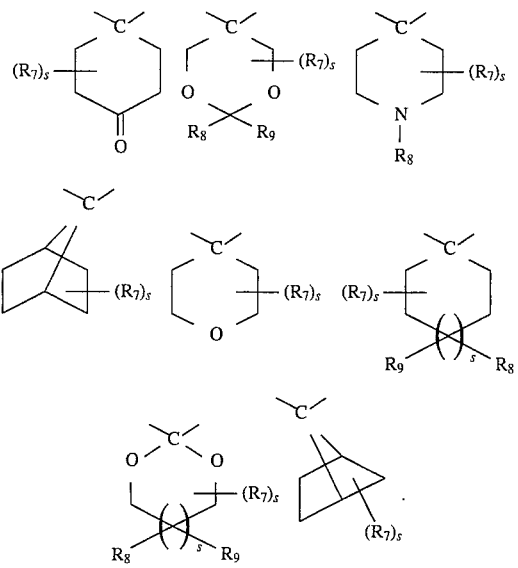

Where —C— denotes the center carbon atom of Z, when Z is —C($R_5$)($R_6$)—; $R_7$ is the same or different and are aryl, alkyl or an alkylene chain completing a 3 to 16 membered ring structure, including fused, spiro, bicyclic and/or tricyclic structures, and the like; $R_8$ and $R_9$ are the same or different at each occurrence and are $R_7$ or hydrogen, and s is the same or different at each occurrence and is 0 to about 3, and the open valencies are substituted with hydrogen atoms.

Also illustrative of these preferred "A" blocks are those comprising recurring units of the formulae:

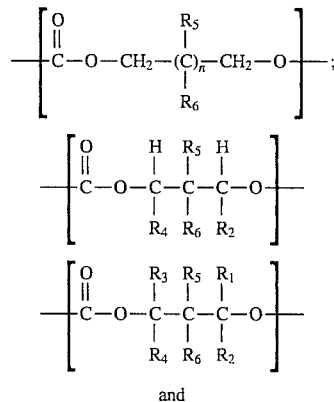

and

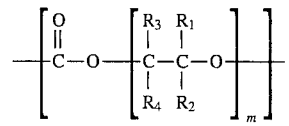

wherein:

$R_1$, $R_2$, $R_3$, and $R_4$, are the same or different at each occurrence and are hydrogen, alkyl such as methyl, ethyl, n-propyl, isopropyl, n-butyl, sec-butyl, n-butyl, neopentyl, and the like; phenyl; phenylalkyl, such as benzyl, phenethyl, and the like; phenyl substituted with one or more alkyl or alkoxy groups, such as tolyl, xylyl, p-methoxyphenyl, m-ethoxyphenyl, p-propoxyphenyl, 1-methoxy 4-methyl phenyl and the like; and alkoxy-alkyl such as methoxymethyl, ethoxymethyl and the like;

$R_5$ and $R_6$ are the same or different at each occurrence and are $R_1$ to $R_4$, alkoxy, alkanoyl, arylcarbonyl, or dialkylamino; or any two of $R_1$ to $R_6$ groups together may form alkylene chain completing 4, 5, 6, 7, 8 or 9 membered alicyclic, spiro, bicyclic and/or tricyclic ring structure, which structure may optionally include one or more non-adjacent divalent carbonyl, oxa, alkylaza or arylaza groups; with the proviso that at least one of $R_1$ to $R_6$ is other than hydrogen; and n and m are the same or different at each occurrence and are 1, 2 or 3.

Particularly preferred for use in the practice of this invention are block copolymers comprising as a "A" block one or more types of recurring units of the formula:

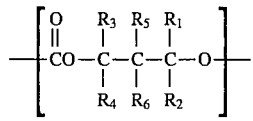

wherein:

$R_1$ to $R_4$ are the same or different and are alkyl, hydrogen, alkoxyalkyl, phenylalkyl, or phenyl substituted with one or more alkyl or alkoxy groups wherein the aliphatic moieties include from 1 to about 9 carbon atoms; and $R_5$ and $R_6$ are the same or different at each occurrence and are selected from the group consisting of $R_1$ to $R_4$ substituents, aryloxy, and alkoxy, or $R_5$ and $R_6$ together may form an aliphatic chain completing a 3 to 10 membered alicyclic, spiro, bicyclic, and/or tricyclic structure which may include one or two non-adjacent divalent carbonyl oxa, alkylaza or arylaza groups with the proviso that at least one of $R_1$ to $R_6$ is other than hydrogen.

In the most preferred embodiments of this invention, the A block of the block copolymer comprises recurring monomeric units of Structure III:

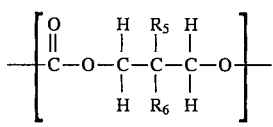

STRUCTURE III wherein:

$R_5$ and $R_6$ are the same or different at each occurrence and are hydrogen, aryl, or alkyl or $R_5$ and $R_6$ together may form a divalent chain completing a 3 to about 10 membered alicyclic, spiro, bicyclic, and/or tricyclic ring structure which may include one or two non-adjacent carbonyl, oxa, alkylaza, or arylaza groups, with the proviso that at least one of $R_5$ and $R_6$ is other than hydrogen.

It is more preferred that the block copolymer comprises the "A" block, recurring monomeric units of Structure III, particularly when $R_5$ and $R_6$ are the same or different and are alkyl, aryl, or a divalent chain forming a 3 to 10 membered, preferably 5 to 7, alicyclic, spiro and/or bicyclic ring structure, which may optionally include one or two non-adjacent oxa, carbonyl, alkylaza or arylaza functional groups. It is particularly preferred that $R_5$ and $R_6$ are the same or different and are aryl or alkylaryl such as, tolyl or phenyl, or lower alkyl having from 1 to about 7 carbon atoms such as methyl, ethyl, propyl, isopropyl, n-butyl, tertiary, butyl, pentyl, neopentyl, hexyl, and secondary butyl.

In the most preferred embodiments where the "A" block has recurring monomeric units of Structure III, $R_5$ and $R_6$ are the same or different and are lower alkyl having from about 1 to about 7 carbon atoms, which do not differ from each other by more than about 2 carbon atoms. In these embodiments, it is particularly preferred that $R_5$ and $R_6$ be the same and be alkyl of about 1 to 2 carbon atoms, and most preferred that $R_5$ and $R_6$ are methyl. Illustrative of the most preferred "A" block are those having recurring monomeric units derived from ring-opened structures of 5,5-dimethyl-1,3-dioxane-2-one, 5,5-diphenyl-1,3-dioxan-2-one, 5,5-diethyl-1,3-dioxan-2-one, 5,5-diisopropyl-1,3-dioxan-2-one, 5,5-dibutyl-1,3-dioxan-2-one, 5,5-dibenzyl-1,3-dioxan-2-one 5,5-dimethoxy-1,3-dioxan-2-one, and other symmetrically substituted cyclic carbonates.

Any combination of starting monomers for the A block (crystalline or semi-crystalline block portions(s)) of the block copolymers of the invention is within the contemplation of the invention, as long as that combination provides a crystalline or partially crystalline block that can form the "hard" sections of the block copolymer of this invention. It is believed that these "hard" sections provide mechanical strength to the resulting block copolymer because they resist stretching when the block copolymer is stretched. For example, block copolymers having such properties are those with their major portion, the crystalline A block depicted in General Structure III, where substituents $R_5$ and $R_6$ of the monomer used in formation of the block are both alkyl, are particularly suited for this purpose.

The block copolymers of the invention also comprise at least one relatively flexible and amorphous "B" block. The flexible amorphous B block may include one or more other types of recurring monomeric units. This component of the copolymers of the invention may vary widely. The only requirement is that the B-block is amorphous and flexible and that it exhibits a glass transition temperature below that of the application temperature. For biomedical implantation devices, the application temperature is preferably less than about 37° C. It is preferred that the B block portion also be bioresorbable.

Suitable B-block are flexible amorphous blocks formed from monomeric units falling within General Structures I and II are especially blocks formed from those units which are less preferred for use in the A-block. In general, homopolymers and random copolymers of at least two types of monomeric units are included for the B-blocks. Another suitable B-block is that formed from the recurring unit of Structures I and III wherein all of the $R_1$ to $R_6$ substituents are hydrogen. Illustrative of still other B recurring monomeric units for use in the B-block are those derived from carbonates, such as the monomeric units included within the scope of General Structures I wherein n is from 0 to 8, as for example, ethylene carbonates, tetramethylene carbonates, trimethylene carbonates, pentamethylene carbonates, and the like. Also illustrative of monomeric units for use in the formation of the "B" block are those which are derived from monomers which polymerize by ring-opening polymerization as for example, substituted and unsubstituted beta, gamma, delta, and omega lactones such as those of the formulae:

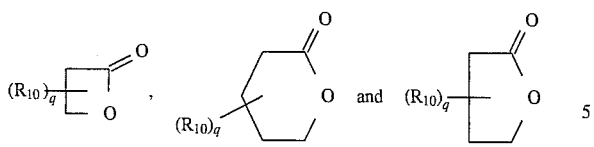 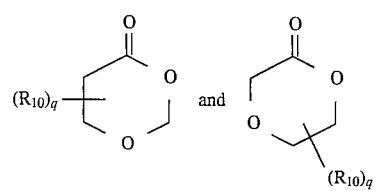

where $R_{10}$ is alkoxy, alkyl or aryl and, q is 0 to about 3 wherein the open valencies are substituted with hydrogen atoms. Such lactones include caprolactones, valerolactones, propiolactones, butyrolactone, and the lactones of other hydroxy carboxylic acids such as 3-hydroxy-2-phenylpropanoic acid, 3-hydroxy-3-phenylpropanoic acid, 4-hydroxybutanoic acid, 3-hydroxybutanoic acid, 3-hydroxy-3-methylbutanoic acid, 5-hydroxypentanoic acid, 3-hydroxy-4-methylheptanoic acid, 4-hydroxyoctanoic acid, 4-hydroxypentanoic acid, and the like; and lactides such as 1-lactide, d-lactide, and d,l-lactide; glycolide; and dilactones such as those of the formulae:

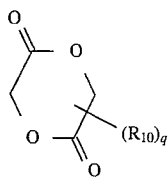

where $R_{10}$ and q are as defined above, such as the dilactones of 2-hydroxycarboxylic acids such as 2-hydroxybutyric acid, 2-hydroxy-2-phenylpropanoic acid, 2-hydroxyl-3-methylbutanoic acid, 2-hydroxypentanoic acid, 2-hydroxy-4-methylpentanoic acid, 2-hydroxyhexanoic acid, 2-hydroxyoctanoic acid, and the like.

Illustrative of still other monomeric units for use in B block are units derived from dioxepanones such as those described in U.S. Pat. No. 4,052,988 and U.K. Patent No. 1,273,733, as for example unsubstituted and substituted dioxepanones of the formulae:

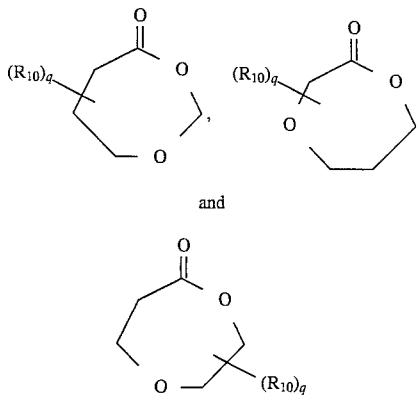

and monomeric units derived from dioxanones such as those described in U.S. Pat. Nos. 3,952,016, 4,052,988, 4,070375, and 3,959,185, as for example, substituted dioxanones and unsubstituted dioxanones of the formulae:

wherein q is as defined above; the open valencies are substituted with hydrogen atoms; and $R_1$ is the same or different at each occurrence and is a hydrocarbyl group such as alkyl, substituted alkyl, aryl or substituted aryl and preferably alkyl containing from 1 to 6 carbon atoms, more preferably alkyl having 1 or 2 carbon atoms;

Suitable "B" blocks also include those derived from cyclic ethers such as 2,4-dimethyl-1,3-dioxane, 1,3-dioxane, 1,4-dioxane, 2-methyl-5-methoxy-1,3-dioxane, 4-methyl-1,3-dioxane, 4-methyl-4-phenyl-1,3-dioxane, oxetane, tetrahydrofuran, tetrahydropyran, hexamethylene oxide, heptamethylene oxide, octamethylene oxide, non-amethylene oxide, and the like.

Still other useful B block components include monomeric units derived from epoxides such as ethylene oxide, propylene oxide, alkyl substituted ethylene oxides such as ethyl, propyl, and butyl substituted ethylene oxide, the oxides of various internal olefins, such as the oxides of 2-butene, 2-pentene, 2-hexene, 3-hexene, and like epoxides; and also including units derived from epoxides with carbon dioxide; and monomeric units derived from orthoesters, orthocarbonates, or substituted or unsubstituted cyclic anhydrides which may optionally include one or more oxa, alkylaza, arylaza and carbonyl groups, such substituted or unsubstituted orthoesters, orthocarbonates and cyclic anhydrides of the formulae:

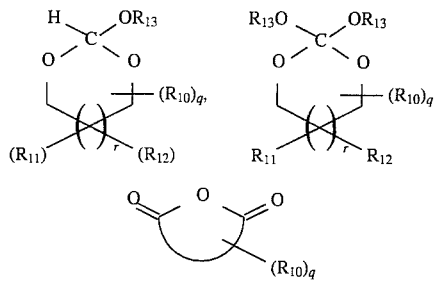

where $R_{10}$, $R_{11}$ and q are as defined above, r is 0 to about 10, and $R_{12}$ and $R_{13}$ are the same or different and are hydrogen, alkyl or aryl.

Monomeric units derived from precursors and derivatives of lactides, lactones, dioxanones, cyclic anhydrides, orthoesters, orthocarbonates, and dioxepanones such as the various hydroxycarboxylic acids, hydroxy substituted oxacarboxylic acids, functionalized esters, substituted or non-substituted diacids such as oxa, alkylaza, arylaza, alkyl or aryl substituted diacids, and acid halide derivatives, and the like can also be used.

Any combination of monomeric units from these would be suitable, as long as the desired flexible characteristics are provided. In the case where certain monomeric units form crystalline or semi-crystalline homopolymers, it is desirable to use as the B-block, copolymers formed from two or more monomeric units in a ratio which leads to an amorphous segment or block. It is conceivable that the copolymer of at least two such monomeric units, which form crystalline or semi-crystalline homopolymers, can provide a soft B-block.

These flexible characteristics are achieved when the B block has a Tg<37° C.

Preferred B block are recurring monomeric units within the scope of Structures I and II, and those derived from lactones, lactides and their precursors, orthoesters, dioxepanones, dioxanones, and orthocarbonates which are bioresorbable and which form a flexible rubbery or soft block. Particularly preferred for use as the B block are those derived from gamma-lactones, delta-lactones and omega-lactones, and their precursor acids such as caprolactone, butyrolactone, valerolactone, 4-hydroxy butanoic acid, 3-hydroxybutanoic acid, and propiolactone; lactides and their precursor acids such as l-lactide, d-lactide, d,l-lactide, 2-hydroxyisobutyric acid, 2-hydroxy-2-phenylpropanoic acid, and the like; dioxepanones, such as 1,5-dioxepan-2-one, and the like; dioxanones, 5,5-dimethyl-1,3-dioxan-2-one, 1,3-dioxane-2-one, 1,4-dioxan-2-one, and the like; carbonates such as trimethylene carbonates, tetramethylene carbonates, dimethylene carbonates and the like; and orthoesters and orthocarbonates. Preferred B-blocks are either homopolymers or random copolymers of at least two units resulting in a soft, rubbery, or amorphous segment.

Most preferred for use in the practice of this invention as B block are those having recurring monomeric units derived from lactones (especially valerolactone, and caprolactone); carbonates (especially trimethylene carbonate); and lactides (especially d,l-lactide) being the units of choice.

Especially preferred are from the random polymerized B-blocks formed from the polymerization of 1,3-dioxan-2-one with d,l-lactide, 5,5-dimethyl-1,1,3-dioxan-2-one with caprolactone and 5,5-dimethyl-1,3-dioxan-2-one with caprolactones, or dioxepanones, and the like.

The block formation and number of recurring units in each block that make up the copolymers of the invention may vary widely according to intended use of the copolymers so formed. For example, diblocks, triblocks, and multiple blocks and the like may be formed. The block copolymers may be used alone or may be blended with other polymers to obtain the desired properties. In the formation of medical devices from the copolymers, such as nerve channels, it is preferred to utilize an "ABA" or "BAB" triblock structure. In these cases, A is the crystalline block and is preferably is formed from the polymerization of 5,5-dimethyl-1,3-dioxan-2-one, and B is the flexible block and is preferably formed from the polymerization of 1,3-dioxan-2-one, or from the random copolymerization of 1,3-dioxan-2-one and d,l-lactide or the random copolymerization of 5,5-dimethyl-1,3-dioxan-2-one and caprolactone, d,l-lactide, and the like.

In addition, for certain applications, end-capping of the block copolymers may be desired. End-capping may be accomplished by conventional means, as for example, acetylation, alkylation, silylation and the like. The copolymers of this invention may also be subjected to chain extension and vains grafting monomeric, oligomeric or polymeric reactions with various reactants. These are techniques well known in the art of polymer science.

In some preferred cases, the B block is formed from a combination of starting monomers as presented above. When the B block is formed from a combination of starting monomers, the relative ratios of one monomer to any of the others may vary widely but are preferably about 20/80 to about 80/20, to allow the B-block to remain amorphous with a relatively low Tg.

The copolymers of this invention are useful in the fabrication of totally or partially bioresorbable medical devices. These devices take many forms depending on intended use. Illustrative of useful devices which may be fabricated from the copolymers of this invention are orthopedic devices such as pins, plates, clamps, screws and plates; vascular implants or supports such as arterial grafts, clips, staples, nerve channels or supports, and the like. Illustrative of still other devices which can be fabricated totally or in part from the copolymers of this invention are devices for tendon and ligament replacement, breast prostheses, dental packs, sponges, hernia patches, burn dressings, absorbent swabs, and the like. Devices fabricated from the copolymers of this invention may be totally bioresorbable or may be fabricated in part from biodurable materials which are relatively resistant to biodegradation. Illustrative of useful biodurable materials are silicone, silicone rubber, polyethylene, polyethylene terephthalate, polyfluoroethylene, polyphosphazene, polyurethane, segmented polyurethane, and the like. Also useful are biodurable metallic substances such as titanium, stainless steel, and alloys such as chrominium-cobalt-molybelenum alloys, titanium-aluminum-vanadium alloys, and the like.

The block copolymers of the invention are particularly suited for use as fibers which fibers can be fabricated into fabrics and other medical devices using conventional techniques. Fibers and fabrics so formed may then be used for a variety of devices. The fibers may be formed from the block copolymers by conventional processes such as dry, gel, melt, and solution or spinning or extrusion or by combination of these processes and the like. These processes are discussed in detail in such sources as Fundamentals of Fiber Formation by Andrzej Ziabicki, Wiley & Sons, 1976.

The block copolymers of the invention are particularly suited to be spun into fibers using a melt-spinning process. In the preferred embodiments, the melt is quenched and, upon exit from the die, oriented to achieve the desired tensile properties. The forming filaments may be melt drawn to finer dimensions under conditions where high orientation is not achieved, if so desired. The orientation drawing following the quench step may proceed immediately or may be done after logging for a period of time under controlled conditions. The oriented filaments may be annealed, heat set, subjected to shrinkage and the like to achieve specific tensile properties.

Generally, oriented fibers show a decreasing modulus with increasing strain prior to the yield point. These materials maintain sufficiently low yield stress, about 0.5 to 0.7 g/denier, at which the fiber shows essentially complete recovery after 20,000 stress cycles during an 8 hour interval, indicating that fabrics constructed of these fibers will not deform its shape when the fibers are subjected to this stress. The present inventors have also discovered that by optimum orientation, annealing and heat setting and, controlled thermal shrinkage, that a 60 to 80% increase in the modulus, e.g., from 4 to 7 g/denier occurs on going from 1 to 3% strain.

The above-described properties of fibers of the invention made from the block copolymers of the invention, renders the fibers particularly suitable to be woven into fabric to be then formed into vascular graft protheses. In general, the static and dynamic compliance of a fabric is determined by its construction, i.e., type of weave, or knit or braid and the fiber tensile and frictional properties. Of particular importance in fiber properties are the modulus and the yield stress or the stress at the elastic limit of the fiber. Natural blood vessels almost invariably have very low initial modulus, less than a 250 KPa, which increases with applied stress. Vascular grafts fabricated according to the present invention are able to achieve this goal of compliancy.

Additionally, there has been an appreciation in the art of vascular protheses, that only a limited number of macrophages infiltrate the implanted biresorbable device. The near neutral or physiological pH local microenvironment of the depolymerising material will probably stimulate very little, if any, macrophages to secrete macrophage derived growth factors which has been known to have a strong influencing affect on fibroblast to form scarring tissue. It has been discovered that vascular protheses fabricated with polycarbonate based block copolymers have these attributes and that the implant induces a minimal fibroblastic reaction while favoring the early differentation of the cellular elements entering the void spaces of the prosthesis which is slowly being bioresorbed. The use of a compliant biodegradable prostheses has been shown to induce the synthesis and secretion of elastin by smooth muscle cells which developed in the void space. These cells tend, with time, to orient themselves longitudinally when being stretched, so that a truly circumferential layer of smooth muscle cells may be achieved within the newly formed arterial wall.

Vascular grafts of the present invention offer advantages in that lipid accumulation within macrophages or myofibroblasts has not been observed. Also, calcification or atheromatous plaque are absent in the regenerated artery. These types of complications have been documented with Dacron protheses available to the art.

The molecular weight of the copolymer may vary widely depending on the use. In general, the molecular weight of the copolymer is sufficiently high to allow its use in the fabrication of medical devices. In the preferred embodiments of this invention where the copolymers are used in the formation of fibers, the copolymers are of "fiber-forming molecular weight." As used herein, a "fiber-forming molecular weight" is a molecular weight which is such that the copolymer can be spun into a fiber. Such molecular weights and their selections are well known in the art.

Useful average molecular weight ranges of the copolymers for use in any particular situation will vary widely depending on the ultimate fiber properties and characteristics it is desired to obtain, such as modulus, tensile strength, bioresorption and biodegradation rates, and the like. In general, copolymer molecular weights useful for forming fibers of the invention are equal to or greater than about 10,000. Preferred average molecular weight ranges are from about 10,000 to about 5,000,000, with a range of from about 20,000 to about 1,000,000 being particularly preferred, and a range of from about 30,000 to about 500,000 being most preferred.

Other polymeric components such as fibers, fillers and binders may be combined with the copolymers prior to and during the formation of fibers or devices, or subsequent to their formation. These include, but are not limited to polymers and copolymers selected from the group consisting of polyesters such as poly(butyleneterephthalate) and poly(ethyleneterephthalate); polyvinylalcohol; polyvinylacetate and partially hydrolyzed forms thereof; hydrogel type polymers such as polyhydroxyethylmethacrylate, poly hydroxypropylmethacrylate, and the like; polysulfones such as polyphenylenesulfone; carbon; silicon carbide; halopolymers such as poly(tetrafluoroethylene) ethylene/tetrafluoroethylene copolymer; polydioxanone; polyglycolid-co-trimethylene carbonates; polylactides; poly-d-lactide; polylactide-co-caprolactone; poly-d,l-lactide; polycaprolactones; polyhydroxybutyrates; poly hydroxyvalerates; polyhydroxybutyrate-co-hydroxyvalerates; polyglycolide; polyurethanes; segmented polyurethanes; polyetherurethanes; polyurethane ureas; silicone rubber; and substances such as fibrin and its powder; natural or processed collagen; mono, di, tri, and polysaccharides; polyethylenes; polyamides; polypropylene; polycarbonates; poly(vinyl fluoride); poly(vinylidene fluoride); poly(vinyl butyral); cellulose such as, carboxylmethyl cellulose, cellulose acetate, ethylcellulose, and the like; ethylene-vinylacetate copolymers and hydrolyzed and partially hydrolyzed forms thereof; polyacrylonitrile; poly-(vinylmethylether); and their derivative co-polymers; and the like.

It is also within the contemplation of the invention that fibers be formed by co-extrusion of different components, organic or inorganic in nature and polymeric or otherwise, together with the polycarbonate fiber materials of the invention. These include, but are not limited to, sheath-core and multiple component, multilayered types of fiber as well as hollow fibers and tubes, especially hollow fibers of multicomponent layered in a concentric manner.

Other components besides polymeric components may be combined with the polymers during or before they are formed into the fibers of the invention, or added to, coated onto and the like, after their formation. These components include substances that will enhance certain of the desired properties of fibers made from the polymers. Among the contemplated classes of such substances are plasticizers, lubricants, antioxidants, stabilizers of all kinds such as stabilizers for UV radiation, heat, moisture, and the like, as well as drugs for treatment of certain disorders or diseases. Materials such as calcium phosphate salts, ceramics, bioresorbable or otherwise, such as calcium hydroxyapatite, Bioglass, and calcium triphosphate may also be combined with the polymer. Components such as certain barium salts to render the fibers and devices formed from them radioopaque are also within the contemplation of the invention. Certain of these fillers, binders, additives and components can be removed or leached from such fibers, at some stage, so that a porous or semi-porous system can be obtained. In addition, gas foaming during the extrusion of the fibers either by gaseous, e.g., $N_2$, He, Ar, Ne, Air, and the like, and/or their combinations, or chemical foaming agents, can be utilized to achieve a porous or somewhat porous fiber structure.

Shapes of the fibers can vary. Shapes such as round, oval, square, rectangular, star shaped, shaped generally characterized as multilobal such as trilobal and hexalobal, semispherical, semitorroidal, semiarched, -bowed, -oblong, and their combinations and the like are included. Cross-sectional dimensions as well as surface properties such as roughness, smoothness, striations on the long axis as well as circumferential ridges and valleys and the like are important with respect to intended use. Hollow fibers are also included. For example, smooth fibers may be important for applications such as vascular graft, woven or knitted from such smooth fibers; striated fibers may be important as ligament or tendon prostheses to encourage certain alignment of cells; hollow fibers and multilobal fibers may be especially important for their use in situations where absorbancy is needed. In addition, applications from sub-denier size fibers to sizes such as ribbons and tapes can be envisaged for those skilled in the art.

The fibers of the present invention are useful in the formation of a variety of devices. The fibers and/or yarns braided or twisted from one or more types of fibers, may be used in the fabrication of various types of articles having medical applications using conventional techniques. For example, such fibers and/or yarns may be woven, braided and/or knitted into fabrics having various structural configurations as for example, tubes, which are knitted, woven or felted, fibrillar products, such as velours. The fibers of this invention are preferably used as sutures or fasteners, and in the fabrication of implantable medical devices such as vascular implants and nerve channels; burn and wound covers; facial substitutes; orthopedic substitutes for bone or bone repair; breast prostheses; tendon and ligament replacements; hernia patches; and the like. Other devices not necessary for implantation purposes can also be envisaged, e.g., cell culture substrates, absorbants or swabs, medicated dressings, gauzes, fabrics, sheets, felts or sponges for hemostasis, dental packs and the like. A good description of the formation of bioresorbable materials in part or in total as matted surgical dressings may be found in U.S. Pat. No. 3,937,223 to Roth.

Particularly useful are woven or knitted fabrics in the form of tubular protheses of varying shapes, lengths and diameters for short or long term implantation. Illustrative of these tubular protheses are vascular grafts, nerve guidance channels, and the like. The particular configuration of such tubular protheses may vary according to the size and shape of the organ to be repaired, and whether the intended repair is to take place in human surgery or in surgery involving other animal species.

The block copolymers of this invention are particularly suited for use in the formation of vascular repair grafts. Such grafts can be fabricated in conventional in configuration as for example as hollow tubes, tubular devices formed from fabrics and the like, using conventional techniques as for example extrusion, weaving, knitting, and the like. In this application, the copolymers of this invention are believed to induce a limited amount of macrophage infiltration into the area of tissue repair which aids in the absorption of the copolymer and other bioresorbable which may be present, and which aids in the formation of organized tissue such as capillaries. For vascular graft applications, the internal diameter commonly found useful is in the range of from about 0.1 mm to about 30 mm.

In the preferred embodiments of the invention, especially for, vascular graft applications, the device is pre-treated to provide a more compliant prostheses. Any conventional method can be used. One of the preferred pre-treatment methods is crimping. Illustrative of useful crimping methods is the method described in U.S. Pat. No. 3,337,673. In this method, the spacing and height can be controlled. The crimping of commercially-available Dacron vascular grafts (including both woven and knitted) was about one millimeter up and millimeter down from the mean diameter of the grafts. Crimping as such can be achieved by this method for the bioresorbable grafts.

In the preferred embodiments, the vascular graft is coated with a bioresorbable coating to improve graft patency. Preferably the desired coating is an amorphous polycarbonate, which has some solubility in a solvent which is a non-solvent for the polymer forming the graft body. In general, the coating is applied to the graft by dissolving the coating polymer in a solvent which is a non-solvent for the graft polymer, and then dipping the graft body into the solution. Illustrative of useful solvents is dimethyl sulfoxide (DMSO), which will dissolve the amorphous polycarbonates which form the coating but not the extruded and more crystalline polymers which form the graft body. The coating solution containing up to about 10% solid can be made with DMSO. For example, a completely clean bioresorbable graft when dipped into a 4.5% solution (six dips, with inversion between each dip) yielded a roughly 25% weight gain. The grafts become slightly stiffer, but the fiber forming the graft body can still be separated down to the monofilaments.

The copolymers of the invention are also suited for use in ligament and tendon replacements. Organized tissue formation is encouraged by the use of the copolymers of this invention, which aids in regenerating ligaments and tendons.

Similarly, the fibers of the invention are also useful in dental and bone repair. In this application, fibers and fabrics formed therefrom may be used in composite structures with or without such materials as calcium hydroxyapatite, Bioglass, calcium triphosphate, drugs, and the like.

Fibers of the present invention may also be used as nerve guidance channels. For example, the fibers may be extruded as hollow tubes with or without wall porosity or may be woven, felted, knitted, braided or the like into nerve guidance channels of many sizes and configurations. U.S. Pat. No. 3,833,002 to Palma discloses various sizes and shapes fabric may be formed into. Lengths of the tubes, internal diameters, and tubular wall thicknesses and wall porosity may vary according to intended use. The length of the tube would ordinarily be commensurate with the size of the nerve gap to be repaired, also allowing extra tubing in which to insert nerve stumps. Particularly useful internal diameters commonly range from about 0.13 mm to 15.00 mm. Tapered tubular prostheses are also within the comtemplation of the invention.

The modulus of the fibers may vary widely depending on the use. Fibers that differ in modulus, although having the same fiber composition, can be obtained by cold draw above Tg or similar processes known to those skilled in the art. For those skilled in the art, it should be appreciated that softened fibers are preferred in certain end applications such as wound dressing, swabs, wound or burn covers, as part of vascular protheses, and the like. Fiber of different or the same polymeric compositions and physical and mechanical properties but differing in denier can be obtained and used or fabricated into fabric that is woven, knitted, velvet, velour, mesh or braided. Staple fibers can be obtained and processed to fabric such as felt, mat and the like. For example, the felted material may be used as, or be part of, skin or wound covers, reinforcements for suturing in surgery, and as aids for hemostasis. Velveted material is particularly suited for use in small caliber blood vessel replacements. Matted fabric may be used, for example, as swabs. Additionally, it should be appreciated that all these forms of fabric and fiber and yarn can be used as slow release drug carriers, not only limited to transdermal, but also used in implantable devices for long or short term procedures.

Thus, for those skilled in the art, it can be appreciated that aside from the polymeric composition and molecular weight and distribution of the copolymers of the invention, processing particulars such as those described above can be profitably utilized or adjusted to achieve varying outcomes in biodegradation or bioresorption rates, hardness, toughness, softness, compliancy, adaptability, amenability to custom fabrication during manufacturing and also in the field during the application of the device. This includes combining fibers of the invention with other bioresorbable fibers, fabrics, or devices. For example, any combination with Vicryl, Maxon, Dexon, PDS (polydioxanone), and other polycarbonate based fibers, and like, is within the contemplation of the present invention.

However, the present inventors do not wish the applications of the fibers of this invention to be limited to totally biodegradable or bioresorbable devices. Fibers or yarns formed from the copolymers of the invention with or without other more biodurable components in the fiber or as part of a device, and/or combinations with other physical objects, are within the contemplation of the invention. These include, but are not limited to, fabrics and/or coated fabrics in a permanent prosthesis or device, implanted into living organisms or otherwise; fabrics and yarns composed of a mix of more biodurable fibers and the fibers of this invention; and the like.

Hollow fibers formed from block copolymers of the present invention are also particularly suited for use as nerve channels for the repair of severed nerves. The particular configuration of such nerve diameters are hollow fibers, preferably, tubes which may vary according to the size and shape of the nerve to be repaired, and whether the intended repair is to take place in human surgery or in surgery involving other animal species. U.S. Pat. No. 3,833,002 to Palma discloses various sizes and shapes that may be employed. Lengths of the hollow fibers or tubes, then internal diameters, and wall thicknesses may vary according to intended use. The length of the hollow fiber or tube would ordinarily be commensurate with the size of the gap to be repaired, also allowing extra tubing in which to insert nerve stumps. The present inventors have found that particularly useful internal diameters commonly range from 0.13 mm to 5.00 mm. It is also desirable to obtain tubes whose wall thicknesses fall within a specific range, such as 0.01 mm to 3.0 mm. A preferred range is 0.05 mm to 1.5 mm in thickness.

The nerve channels may be formed from the block copolymers of the invention by any conventional techniques such as melt extrusion, solution extrusion, gel extrusion, other possible combinations of the above processes, and the like. However, it is particularly useful to employ an extrusion process wherein the hollow fiber or tube dimensions may be carefully controlled by the extruding die dimensions, differential gas pressure between inner and outer surfaces of the tube, melt draw down and subsequent orientation processes. Die dimensions are easily selected by consideration of the inner and outer diameters of the nerve channel, die swell, extrusion rates, orientation in the melt and rubbery state. For nerve channels having the characteristics of the desirable dimensions and evenness, the usual procedure is to pressurize the tube with an inert gas to prevent collapsing the differential gas pressure is preferably maintained at about 0 to about 0.02 atm, most preferably 0 to about 0.004 atm. The melt draw down may be controlled by the ratio of average exit velocity out of the die and the take up velocity. The exit velocity for a given die and polymer melt viscosity is controlled by the extrusion pressure. Orientation is preferably effected by the ratio of speeds of two sets of rollers. Often a draw pin or heated surface is present between the rollers to stabilize the orientation process.

Similarly, hollow fibers may be used as blood conduit replacements or prostheses. The range of internal diameter can vary widely depending on the vessel to be replaced; particularly useful range are commonly found to be 0.3 mm to 30 mm. For these applications, hollow fibers or tubes with or without wall porosity are contemplated.

Other applications of hollow fibers as implantable devices may include fallopian tube ducts, sperm ducts, or the like. In particular, hollow fibers or tubings of this invention may be used as devices where bio- or blood-compatibility is most desired, e.g., tubings for transferring blood or other bodily fluids from one place to another.

It must be stressed that the block copolymers can be extruded as a hollow fiber or tube which behaves as a thermoplastic elastomer and which will not collapse upon pinching. This is especially important in the case of nerve channels or other applications, such as vascular graft, where a conduit is needed. Also it will allow suture needles to go through the wall without ripping of the tube or hollow fiber which will also have the strength to be sutured properly without tearing.

The following are more specific embodiments of the invention, but are not to be considered limitative thereof.

EXAMPLES

Hollow Fiber Preparation

The fabrication of polycarbonates to nerve channel tubes, or hollow fibers, based on DMTMC with TMC or caprolactone in an ABA or BAB triblock structure where A is a DMTMC block and B, the rubbery block, is a copolymer of DMTMC with TMC or DMTMC with caprolactone, was evaluated using the Instron Rheometer as a ram extruder and a tube in orifice type die to extrude the tube. The hollow fiber or tube dimensions were controlled by the die dimensions, differential gas pressure between the inner and outer surfaces of the tube, melt draw down and subsequent orientation processes. Range of diameters were about 0.5 to about 3 mm internal diameter, with a significant wall thickness to provide rigidity and strength for implantation into an animal or human.

Dies having tube outer diameters of about 1.5 mm and orifices ranging from 2.2–2.5 mm were used without an appreciable applied pressure differential. There was significant die swell during extrusion which provided inner tube diameters greater than 3 mm.

Example 1

ABA Block copolymer of
5,5-Dimethyl-1,3-dioxan-2-one (DMTMC) and
Caprolactone (CL); B=1:1 DMTMC:CL,
A=DMTMC, A:B=80:20

An oven-dried, silanized glass 150 mL resin flask was equipped with mechanical stirrer with a teflon paddle, argon inlet, a serum cap on one port, and a glass stopper on the remaining port. To the flask were added freshly dried and purified DMTMC (4.15 g, 31.9 mmol), caprolactone (3.64 g, 31.9 mmol), and 2,2-dimethylpropanediol (7.5 mg, 0.072 mmol). The flask was evacuated and filled with argon several times, then immersed in an oil bath at 160° C. Stirring was initiated, and after 5 minutes, 25 µL of of a 1.0M solution of stannous octoate in toluene, the catalyst solution, was added. Noticeable thickening occurred in about 20 minutes; after 1.5 hours, the oil bath was lowered and the flask was evacuated briefly to remove some of the unreacted monomers that had condensed on the upper part of the flask. Heating was resumed and DMTMC (6.64 g, 51 mmol) was added, followed by an additional 25 µL of the catalyst solution. After an additional 10 minutes, more DMTMC (26.57 g, 204.2 mmol) was added and the mixture stirred with continued heating at 160° C. In about 30 minutes, the mixture became too thick to be stirred, but heating was continued for an additional hour, when the polymerization was terminated.

The viscous polymer was scooped out of the flask (37.8 g recovery), dissolved in dioxane (300 mL), and precipitated in a blender into water (1200 mL). The polymer was then washed twice in the blender with water, filtered and dried in vacuum at 45° C. overnight. Yield: 32.9 g (80%). Weight average molecular weight =121,000 by GPC (THF solvent).

Example 2

ABA Block Copolymer of DMTMC and Caprolactone (CL); B=1:1 DMTMC:CL, A=DMTMC, A:B=70:30

A polymerization similar to Example 1 was carried out in a 1 liter resin flask. The first (B-block) stage employed 39.04 g (300 mmol) DMTMC, 34.24 g (300 mmol) caprolactone, 30 mg (0.29 mmol) 2,2-dimethylpropanediol, and 150 µL of 1M stannous octoate in toluene. After 2 hours heating at 160° C., the reactor was evacuated briefly and all of the remaining DMTMC (182.2 g, 1400 mmol) was added at once. An additional 150 µL of catalyst solution was added and stirring continued for 2.5 hours until the polymer became too viscous to stir. Heating at 160° C. was continued overnight, then the polymer was removed from the flask, dissolved in 2.5 L dioxane and precipitated in batched into water (ca 10 L). After washing and drying as before, the polymer weighed 226 g (89%). Weight average molecular weight=110,000 by GPC (THF); caprolactone content by $^1$H NMR=17% (theory 15%).

Example 3

ABA Block Copolymer of DMTMC and Trimethylene Carbonate (TMC); B=TMC, A=DMTMC, A:B=80:20

A polymer was prepared as in Example 1, except that the initial charge consisted of TMC (6.12 g, 60 mmol) and 2,2-dimethylpropanediol (10.3 mg, 0.1 mmol). The flask was immersed in an oil bath at 160°, then after five minutes 25 µL of 1M stannous octoate was added. In 30 minutes the TMC had polymerized to a viscous material; this was sampled and then DMTMC (31.12 g, 240 mmol) was added all at once. The poly(TMC) prepolymer gradually dissolved in the DMTMC and the mixture became homogeneous and eventually very viscous. After a total time of 3.5 hours, the reaction was stopped and worked up as in Example 1. Yield: 27.7 g (74%). Trimethylene carbonate content by $^1$H NMR= 23.6% (theory 20%). Weight average molecular weight by GPC (THF) of prepolymer=37,000, of final polymer=105,000. Differential scanning calorimetry (DSC) of the final polymer showed a glass transition temperature (Tg) of 0° C. and a melting temperature of 71° C.

Example 4

Block Copolymerization of DMTMC and TMC in Xylene Solution

In an oven-dried 100 mL resin flask were combined DMTMC (7.81 g, 60 mmol), TMC (6.13 g, 60 mmol) and dimethylpropanediol (3 mg). The flask was evacuated to 0.1 mm Hg for ten minutes, then filled with dry argon. Xylene (15 mL), dried by distilling from sodium metal, was added to the flask by syringe, then the flask was immersed in an oil bath at 150° C. After stirring for five minutes, tin octoate (25 mL of a 1.0M solution in toluene) was added. The solution became very viscous over a two hour period; a sample (ca. by GPC showed a weight average molecular weight of 142,000. The solution was precipitated into methanol, the polymer washed with methanol and dried. NMR analysis of the precipitated sample showed a TMC content of 51% and DMTMC content of 49%. From the carbonyl carbon region of the 100 MHz carbon spectrum, it was determined that the carbonate groups of the polymer consisted of 27% DMTMC-DMTMC linkages, 28% TMC-TMC linkages and 45% DMTMC-TMC linkages.

Additional DMTMC (10.41 g, 80 mmol) was added to the flask and the mixture stirred at 150° C. for an additional 3.5 hours. The polymer was dissolved in dioxane 350 mL, precipitated into methanol (1100 mL), washed with additional methanol and dried. Yield: 19.0 g (78%). Weight average molecular weight=168,00–by GPC (THF). TMC content=32% by proton NMR (theory=30%). The carbonyl region of the spectrum shows 48% DMTMC-DMTMC linkages, 36% DMTMC-TMC linkages and 16% TMC-TMC linkages; calculated values assuming only DMTMC-DMTMC linkages are formed in the second stage: 50% DMTMC-DMTMC, 31% DMTMC-TMC, and 19% TMC-TMC.

Example 5

The block copolymer of DMTMC and caprolactone listed as Sample 2 in Table I was melt extruded into monofilament fiber at 195° C. The fibers were drawn at room temperature and good fiber characteristics were found as documented in Table III as 2A–2G.

Example 6

The block copolymer of DMTMC and caprolactone listed as Sample 3 in Table I was melt extruded and moderately drawn to limit the tensile modulus. Low modulus fibers of good strength and high elongations were achieved as shown in Table III as entries 3A–3B.

Example 7

The block copolymer of DMTMC and caprolactone listed as Sample 5 in Table I was melt spun and drawn at room temperature at a number of low draw ratios to limit the modulus. Good fiber strengths at these low moduli were achieved as shown in Table III as 5A–5E.

Example 8

Fiber 5D from Table III was heat set on a heated block at 74°–77° C. at 100 ft/min under a 2% overdraft and at draw ratios of 1.06, 1.22, 1.3 and 1.42. These fibers are listed as 5E-1 through 5E-5, respectively, in Table III.

Example 9

Sample 10 from Table II, an A-B-A block copolymer of DMTMC (A block) and a 50/50 random copolymer of DMTMC and TMC (B block) was extruded into hollow fibers or tubes ranging from 0.5 to 2 mm in diameter using a tube-in-orifice die. The tubes were still somewhat tacky when dry, although they could be easily handled when wet. Tubes having 0.2 mm wall thickness for 1 mm OD would spring open when pressed together.

Example 10

Sample 12 from Table II was an A-B-A block copolymer of DMTMC (A block) and a 50/50 copolymer of DMTMC and TMC (B block). Because of its high molecular weight and related high melt viscosity, the polymer melt fractured when extruded. Satisfactory tubes could, however, be extruded at 220° C. The melt strength of this BAB structure was significantly lower than the A-B-A structure in Example 9. The material also is more tacky than the ABA structure. However, tubes pinched close would reopen, indicating that a high molecular weight of the A block is desirable. Tube inner diameters of 0.5 to 3 mm were achieved.

Example 11

An A-B-A block copolymer was made, Sample 13, Table II, where the A-block was DMTMC, and the B-block was a 50/50 random copolymer of DMTMC and TMC, with the B block molecular weight being the highest in the series of A-B-A polymers of DMTMC—A Blocks. This material extruded well at 180° C. and tube sizes ranging from inner diameters of 0.5 to 3 mm was achieved. Tack was lower than previous examples, and the dry tubes reopened when pinched closed.

Example 12

Tendon and Ligament Replacement Devices

A. Uniaxial towed fiber device

A bundle of well-aligned fibers, roughly with cross-sectional dimensions of 5–6 mm by 0.4–0.5 mm and with a length of 45 cm are fastened onto two surgical needles. The device is cleaned with 0.05% Triton X-100 in 50% ethanol-water, then rinsed six times with water, and finally rinsed with absolute alcohol. The operation is performed inside a class 100 laminar flow hood from the cleaning of the device up to and including packaging of the device in sterilization bags. Standard cold cycle ethylene oxide is used to sterilize these devices.

The device of this size is useful for tendon or ligament replacement in small animals, e.g., the Achilles tendon in rabbits.

B. Braided and crocheted fabric devices

Six yarns of twisted fibers are braided together to form a strand of fabric, 45 mm in length, and with cross-sectional dimensions of 1 mm by 6 mm. Similarly, yarns are crocheted into devices of various cross-sectional diameters and lengths, depending on the end-application. These fabrics are cleaned as discussed above, and are to be used as replacement devices for ligaments and tendons in small animals.

TABLE I

ABA BLOCK COPOLYMERS OF CAPROLACTONE (CL) AND DIMETHYLTRIMETHYLENE CARBONATE (DMTMC)

| Sample Number | A Block | B Block | A:B Ratio | Quantity Isolated | Yield (%) |
|---|---|---|---|---|---|
| 1 | DMTMC | DMTMC:CL 3:1 | 70:30 | 20.0 g | 65 |
| 2 | DMTMC | DMTMC:CL 4:1 | 85:15 | 41.3 g | 87 |
| 3 | DMTMC | DMTMC:CL 1:1 | 80:20 | 32.9 g | 80 |
| 4 | DMTMC | DMTMC:CL 3:1 | 77:23 | 33.4 g | 81 |
| 5 | DMTMC | DMTMC:CL 1:1 | 70:30 | 32.1 g | 79 |
| 6 | DMTMC | DMTMC:CL 1:1 | 70:30 | 210.4 g | 82 |
| 7 | DMTMC | DMTMC:CL 1:1 | 70:30 | 223.7 g | 88 |
| 8 | DMTMC | DMTMC:CL 1:1 | 70:30 | 226.6 g | 89 |
| 9 | DMTMC | DMTMC:CL 1:1 | 70:30 | Blended | |

| Sample Number | GPC Main Wt Av MW | Peak Disp. | GPC Overall Wt Av MW | Disp. |
|---|---|---|---|---|
| 1 | 47,300 | 2.55 | 50,400 | 4.63 |
| 2 | 118,000 | 3.70 | 181,000 | 47.60 |
| 3 | 140,000 | 4.20 | 121,000 | 33.60 |
| 4 | 92,000 | 3.50 | 93,400 | 13.15 |
| 5 | 132,000 | 2.80 | 152,000 | 14.30 |
| 6 | 67,100 | 1.90 | 67,100 | 1.90 |
| 7 | 83,800 | 1.68 | 83,800 | 1.68 |
| 8 | 110,000 | 2.90 | 113,000 | 19.50 |
| 9 | 89,600 | 2.90 | 112,500 | 16.50 |

TABLE II

ABA BLOCK COPOLYMERS OF TRIMETHYLENE CARBONATE (TMC), d,l-lactic acid(LA) AND DIMETHYLTRIMETHYLENE CARBONATE (DMTMC)

| Sample Number | A Block | B Block | A:B Ratio | Quantity Isolated | Yield (%) |
|---|---|---|---|---|---|
| 10 | DMTMC | TMC:DMTMC 1:1 | 25:75 | 33.6 g | 88 |
| 11 | DMTMC | TMC:DMTMC 1:1 | 35:65 | 33.4 g | 75 |
| 12 | DMTMC | TMC:DMTMC 1:1 | 65:35 | 35.8 g | 80 |
| 13 | DMTMC | TMC:DMTMC 1:1 | 40:60 | 36.0 g | 82 |
| 14 | DMTMC | TMC:DMTMC 1:1 | 50:50 | 30.5 g | 83 |
| 15 | DMTMC | TMC:d,1-LA 1:1 | 80:20 | 29.8 g | 82 |
| 16 | DMTMC | TMC:DMTMC 1:1 | 60:40 | 17.3 g | 46 |
| 17 | DMTMC | TMC:DMTMC 1:1 | 60:40 | 29.9 g | 80 |
| 18 | DMTMC | TMC | 60:40 | 30.0 g | 84 |
| 19 | DMTMC | TMC | 80:20 | 27.7 g | 74 |
| 20 | DMTMC | TMC | 70:30 | 30.3 g | 83 |

| Sample Number | GPC Main Wt Av MW | Peak Disp. | GPC Overall Wt Av MW | Disp. | Tg | Tm | TMC by NMR % (Theory) |
|---|---|---|---|---|---|---|---|
| 10 | 48,400 | 6.20 | 48,500 | 3.20 | | | (38) |
| 11 | 112,000 | 8.06 | 92,000 | 2.30 | | | (33) |
| 12 | 124,000 | 4.34 | 159,000 | 5.48 | | | (18) |
| 13 | 196,000 | 4.90 | 194,000 | 20.80 | | | (30) |
| 14 | 64,500 | 3.60 | 65,100 | 22.00 | | | (25) |
| 15 | 102,000 | 2.40 | 101,700 | 4.28 | | | (10) |
| 16 | 64,000 | 4.70 | 83,100 | 22.40 | −2° C. | 71° C. | 31.6 (20) |

TABLE II-continued

ABA BLOCK COPOLYMERS OF
TRIMETHYLENE CARBONATE (TMC), d,l-lactic acid(LA)
AND DIMETHYLTRIMETHYLENE CARBONATE (DMTMC)

| 17 | 87,000  | 4.80 | 99,000  | 23.00 | 3° C.   | 60° C. | 22.0 (20) |
| 18 | 53,100  | 3.36 | 61,800  | 10.50 | −12° C. |        | 44.0 (40) |
| 19 | 113,000 | 3.60 | 105,000 | 22.60 | 0° C.   | 71° C. | 23.6 (20) |
| 20 | 51,500  | 4.10 | 84,800  | 24.30 | −3° C.  | 59° C. | 31 (30)   |

TABLE III

Tensile properties of Monofilament Fiber (tested at 23° C., 50% RH at 100% extension rate with 5 inch gauge length yarn samples average of ten or more measurements).

| Sample | Denier | Tensile Modulus grams/denier | Tensile Strength grams/denier | Ultimate Elongation % |
|---|---|---|---|---|
| 2A   | 100 | 26 | 1.3 | 244 |
| 2B   | 12  | 83 | 4.9 | 19  |
| 2C   | 14  | 90 | 4.8 | 24  |
| 2D   | 18  | 98 | 3.6 | 34  |
| 2E   | 15  | 77 | 3.9 | 25  |
| 2F   | 12  | 89 | 4.6 | 16  |
| 2G   | 16  | 76 | 4.1 | 38  |
| 3A   | 74  | 26 | 3.6 | 66  |
| 3B   | 60  | 31 | 4.2 | 61  |
| 5A   | 49  | 33 | 4.6 | 30  |
| 5B   | 59  | 13 | 3.9 | 66  |
| 5C   | 53  | 22 | 4.6 | 54  |
| 5D   | 55  | 10 | 4.0 | 49  |
| 5E   | 46  | 19 | 4.4 | 54  |
| 5E-1 | 52  | 9  | 4.3 | 57  |
| 5E-2 | 48  | 15 | 4.4 | 49  |
| 5E-3 | 42  | 30 | 5.2 | 34  |
| 5E-4 | 41  | 26 | 5.2 | 31  |
| 5E-5 | 47  | 32 | 5.2 | 23  |

What is claimed is:

1. A fiber comprising a biodegradable block copolymer consisting essentially of at least one crystalline or semi-crystalline rigid "A" block, and at least one flexible, amorphous "B" block, said "A" block formed from at least one type of recurring monomeric unit of the following General Structure I or II:

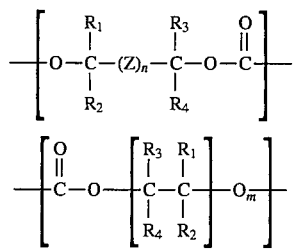

wherein
Z is

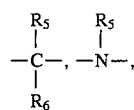

or a combination thereof
where Z is selected such that there are no adjacent heteroatoms;

n and m are the same or different at each occurrence and are integers from 1 to 8;

$R_1$, $R_2$, $R_3$, and $R_4$ are the same or different at each occurrence and are hydrogen, alkoxyaryl, aryloxyaryl, arylalkyl, alkylarylalkyl, arylalkylaryl, alkylaryl, arylcarbonylalkyl, aryloxyalkyl, alkyl, aryl, alkylcarbonylalkyl, cycloalkyl, arylcarbonylaryl, alkylcarbonylaryl, alkoxyalkyl, or aryl or alkyl substituted with one or more substituents selected from the group consisting of alkyl, aryl, alkoxy, aryloxy, dialkylamino, diarylamino or alkylarylamino;

$R_5$ and $R_6$ are the same or different and are $R_1$, $R_2$, $R_3$, $R_4$, dialkylamino, diarylamino, alkylarylamino, alkoxy, aryloxy, alkanoyl, or arylcarbonyl; or any two of $R_1$ to $R_8$ substituents together may form an alkylene chain completing a 3, 4, 5, 6, 7, 8 or 9 membered alicyclic, fused, spiro, bicyclic and/or tricyclic ring system, which system may optionally include one or more non-adjacent carbonyl, oxa, alkylaza or arylaza groups; and said "B" block is different from said A-block and consists of at least one type of recurring unit derived from monomers selected from the group consisting of lactones, hydroxycarboxylic acids, lactides, epoxides, cyclic ethers, dioxanones other than carbonates, polyols, orthoesters, carbonates, and epoxides/$CO_2$.

2. An implantable medical device fabricated totally or in part from the fiber of claim 1.

3. An implantable medical device which is tubularly woven totally or in part from the fiber of claim 1.

4. A medical device according to claim 3 wherein said device is selected from the group consisting of nerve channels and vascular grafts.

5. The fiber of claim 1 wherein $R_1$, $R_2$, $R_3$, $R_4$, $R_5$ and $R_6$ are the same or different and are selected from the group consisting of hydrogen, alkyl, cycloalkyl, alkoxyalkyl, aryloxyalkyl, aryloxyaryl, arylalkyl, and aryl and arylalkyl groups substituted with one or more alkyl, alkoxy and alkoxyalkyl groups.

6. The fiber of claim 5 wherein $R_1$, $R_2$, $R_3$, $R_4$, $R_5$ and $R_6$ are the same or different and are selected from the group consisting of phenyl, hydrogen, alkyl, cycloalkyl, alkoxyalkyl, phenylalkyl, and phenyl and phenyl-alkyl substituted with one or more alkyl or alkoxy groups.

7. The fiber of claim 6 wherein said a block is a recurring unit wherein Z is selected from the group consisting of:

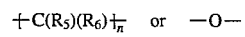

wherein n is 1, 2 or 3.

8. The fiber of claim 7 wherein n the a block is of the Structural Formula I, n is 1 and z is:

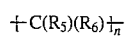

9. The fiber of claim 6 wherein said A block comprises recurring moieties selected from the group consisting of:

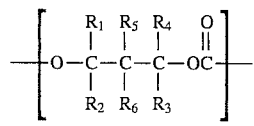

wherein:

$R_1$, $R_2$, $R_3$ and $R_4$ are hydrogen; and $R_5$ and $R_6$ are the same or different and are hydrogen, alkyl, phenyl, phenylalkyl, alkoxyalkyl, phenyl substituted with one or more alkyl or alkoxy groups; alkoxy, alkanoyl, or dialkylamino.

10. The fiber of claim 9 wherein $R_5$ and $R_6$ are the same or different and are phenyl, phenylalkyl, alkylphenyl or alkyl.

11. The fiber of claim 10 wherein $R_5$ and $R_6$ are the same or different and are alkyl or phenyl.

12. The fiber of claim 11 wherein $R_5$ and $R_6$ are the same.

13. The fiber of claim 12 wherein $R_5$ and $R_6$ are alkyl.

14. The fiber or claim 13 wherein $R_5$ and $R_6$ are lower alkyl of from about 1 to 7 carbon atoms.

15. The fiber of claim 14 wherein $R_5$ and $R_6$ methyl.

16. The fiber of claim 13 wherein said B-block comprises recurring monomeric units derived from delta lactones, lactides, or trimethylene carbonate.

17. The copolymer of claim 16 wherein said B-block contains only one type of recurring monomeric unit.

18. The fiber of claim 16 wherein said B-block contains more than one type of recurring monomeric unit which are randomly distributed throughout said B-block, or distributed said B-block or in blocks.

19. The fiber of claim 17 wherein said B-block is derived from caprolactone or trimethylene carbonate and said "A" block is derived from 5,5-dimethyl-1,3-dioxane-2-one.

20. The fiber of claim 18 wherein said A block is derived from 5,5-dimethyl-1,3-dioxan-2-one and said B-block is derived from a copolymer derived from trimethylene carbonate and 5,5-dimethyl-1,3-dioxan-2-one.

21. An implantable medical device which is a fabric woven totally or in part from fibers of claim 1.

22. An implantable medical device comprising a body, said body comprising at least one portion formed from a biodegradable block copolymer consisting essentially at least one crystalline or semi-crystalline rigid "A" block, and at least one flexible, amorphous "B" block, said "A" block formed from at least one type of recurring monomeric unit of the following General Structure I or II:

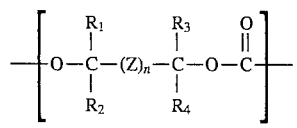   Structure I

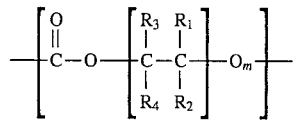   Structure II wherein:

Z is

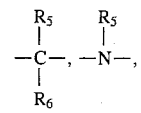

or a combination thereof where Z is selected from such that there are no adjacent heteroatoms;

n and m are the same or different at each occurrence and are integers from 1 to 8;

$R_1$, $R_2$, $R_3$, and $R_4$ are the same or different at each occurrence and are hydrogen, alkoxyaryl, aryloxyaryl, arylalkyl, alkylarylalkyl, arylalkylaryl, alkylaryl, arylcarbonylalkyl, aryloxyalkyl, alkyl, aryl, alkylcarbonylalkyl, cycloalkyl, arylcarbonylaryl, alkylcarbonylaryl, alkoxyalkyl, or aryl or alkyl substituted with one or more substituents selected from the group consisting of alkyl, aryl, alkoxy, aryloxy, dialkylamino, diarylamino or alkylarylamino;

$R_5$ and $R_6$ are the same or different and are $R_1$, $R_2$, $R_3$, $R_4$, dialkylamino, diarylamino, alkylarylamino, alkoxy, aryloxy, alkanoyl, or arylcarbonyl; or any two of $R_1$ to $R_6$ substituents together may form an alkylene chain completing a 3, 4, 5, 6, 7, 8 or 9 membered alicyclic, fused, spiro, bicyclic and/or tricyclic ring system, which system may optionally include one or more non-adjacent carbonyl, oxa, alkylaza or arylaza groups; and said "B" block is different from said A-block and consists of at least one type of recurring unit derived from monomers selected from the group consisting of lactones, hydroxycarboxylic acids, lactides, epoxides, cyclic ethers, dioxanones other than carbonates, polyols, orthoesters, carbonates, and epoxides/$CO_2$.

23. A medical device according to claim 22 which further comprises a biodurable portion.

* * * * *